US00PP22175P2

(12) United States Plant Patent
Catt

(10) Patent No.: US PP22,175 P2
(45) Date of Patent: Oct. 4, 2011

(54) ***CARYOPTERIS* PLANT NAMED 'GOLD GIANT'**

(50) Latin Name: ***Caryopteris*×*clandonensis***
Varietal Denomination: Gold Giant

(76) Inventor: Peter Catt, Liss (GB)

( * ) Notice: Subject to any disclaimer, the term of this patent is extended or adjusted under 35 U.S.C. 154(b) by 0 days.

(21) Appl. No.: 12/803,363

(22) Filed: Jun. 25, 2010

Related U.S. Application Data

(60) Provisional application No. 61/269,884, filed on Jul. 1, 2009.

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette Para

(57) ABSTRACT

A new and distinct cultivar of *Caryopteris* named 'GOLD GIANT' that is characterized by strong upright habit, mid-deep blue flowers, and bright golden yellow foliage throughout the season. In combination these traits set 'GOLD GIANT' apart from all other existing varieties of *Caryopteris* known to the inventor.

2 Drawing Sheets

Genus: *Caryopteris.*
Species: ×*clandonensis.*
Denomination: 'GOLD GIANT'.

BACKGROUND OF THE INVENTION

This application claims the benefit of priority under 35 U.S.C. 119(e) of U.S. Provisional Application No. 61/269,884 filed on Jul. 1, 2009, entitled *Caryopteris* Plant Named 'GOLD GIANT'.

The present invention relates to a new and distinct cultivar of *Caryopteris,* also known as blue-mist or bluebeard, which is grown as an ornamental shrub for use in the garden and landscape. The new invention from the family Verbenaceae is known botanically as *Caryopteris*×*clandonensis* and will be referred to hereinafter by the cultivar name 'GOLD GIANT'.

'GOLD GIANT' resulted from a long term breeding program within the genus *Caryopteris* which the inventor commenced in 1990 and carried out at the inventor's nursery in Hampshire, United Kingdom. 'GOLD GIANT' is a seedling selection derived from the deliberate open cross-pollination of the seed parent, an individual *Caryopteris clandonensis* 'Worcester Gold' (unpatented) and the pollen parent, an individual *Caryopteris clandonensis* 'Worcester Gold' (unpatented).

To initiate the breeding process the inventor isolated container-grown plants of *Caryopteris* 'Worcester Gold' on a nursery bench which was isolated from all other *Caryopteris* in the nursery. Following successful cross-pollination the resulting seed was collected by the inventor and sown in the autumn of 2000, with the intention of producing new seedlings with desired traits. The inventor selected 'GOLD GIANT' in 2004 based on the criteria of vigor, habit, and foliage color.

The distinguishing traits of 'GOLD GIANT' are strong upright habit, profusions of mid-deep blue flowers from early summer through fall, and bright golden yellow foliage throughout the season, with dark contrasting stems. 'GOLD GIANT' is vigorous, growing to 60 cm. in height and 76 cm. in width during the first year, reaching 90 cm-110 cm. in height and 90 cm-110 cm. in width at maturity. Cultural requirements include full sun, well-draining soil and minimal to moderate water. 'GOLD GIANT' is hardy to USDA Zone 6. Once established, 'GOLD GIANT' is drought tolerant and heat tolerant.

The closest comparison plant known to the inventor is *Caryopteris* 'Worcester Gold'. The comparison plant exhibits pale summer foliage, wispy open habit, and narrow leaves. The new *Caryopteris* variety 'GOLD GIANT' is distinguishable from the comparison plant by strong upright habit, broad leaves, and bright golden yellow foliage that remains so throughout the season without fading.

'GOLD GIANT' was first asexually reproduced by the inventor in Greatham, Hampshire, United Kingdom, in 2005. Asexual propagation was accomplished using semi-ripe stem cuttings. Since that time under careful observation, the distinguishing characteristics of 'GOLD GIANT' have been determined stable and uniform, and to reproduce true to type in successive generations of asexual propagation.

SUMMARY OF THE INVENTION

The distinguishing characteristics of the new *Caryopteris* cultivar named 'GOLD GIANT' are as follows. In combination these traits set 'GOLD GIANT' apart from all other existing varieties of *Caryopteris* known to the inventor. 'GOLD GIANT' has not been tested under all possible conditions, and phenotypic differences may be observed with variations in environmental, climatic, and cultural conditions without however any variance in genotype.

1. 'GOLD GIANT' exhibits strong upright habit.
2. The stems of 'GOLD GIANT' are dark brown to black in color.
3. The foliage of 'GOLD GIANT' is bright golden yellow.
4. The golden yellow color of the foliage of 'GOLD GIANT' persists through the summer and into fall without fading.
5. The leaves of 'GOLD GIANT' are irregularly toothed.
6. The flowers of 'GOLD GIANT' are mid-deep blue in color.

7. At maturity, a plant of 'GOLD GIANT' achieves a height in the range of 90 cm -110 cm. and a spread in the range of 90 cm-110 cm.
8. 'GOLD GIANT' is hardy to USDA Zone 6.

BRIEF DESCRIPTION OF THE DRAWINGS

The accompanying color drawings illustrate the overall appearance of the new *Caryopteris* cultivar named 'GOLD GIANT' showing the color of its foliage and flowers as true as is reasonably possible to obtain in color reproductions of this type.

Color in the drawings may differ from color values cited in the detailed botanical description, which accurately describe the actual color of the new variety 'GOLD GIANT'.

Figure 1:
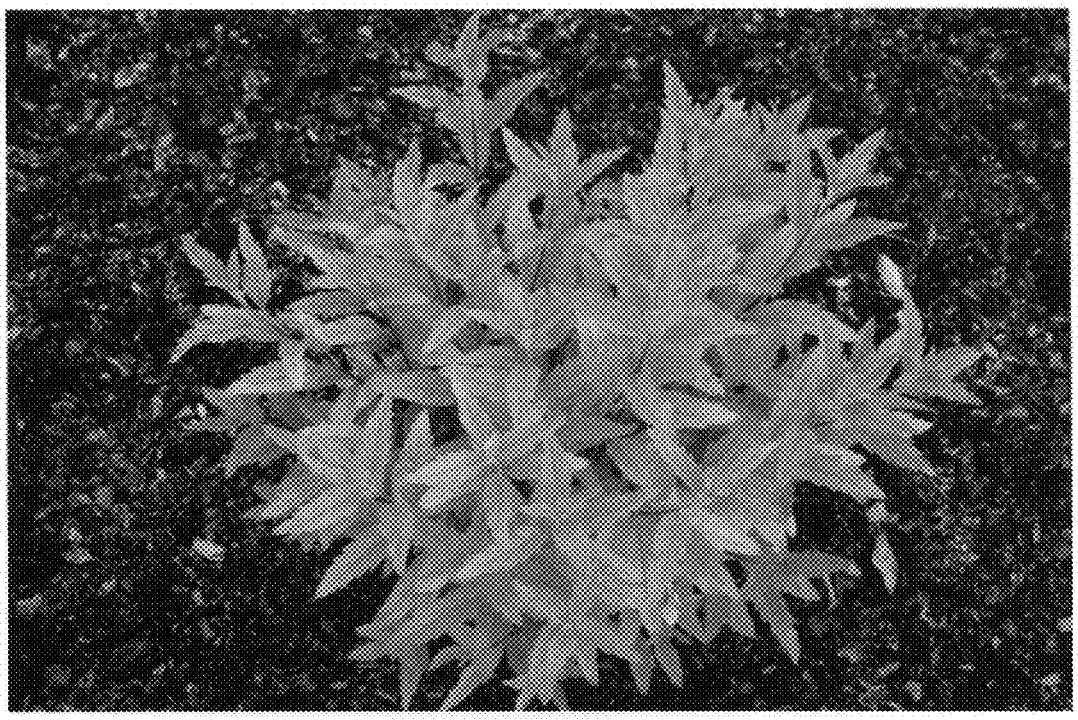

The drawing labeled as FIG. 1 depicts an overhead view of a one-year-old plant of 'GOLD GIANT' growing in a 1-liter container out-of-doors in Hampshire, United Kingdom.

Figure 2:
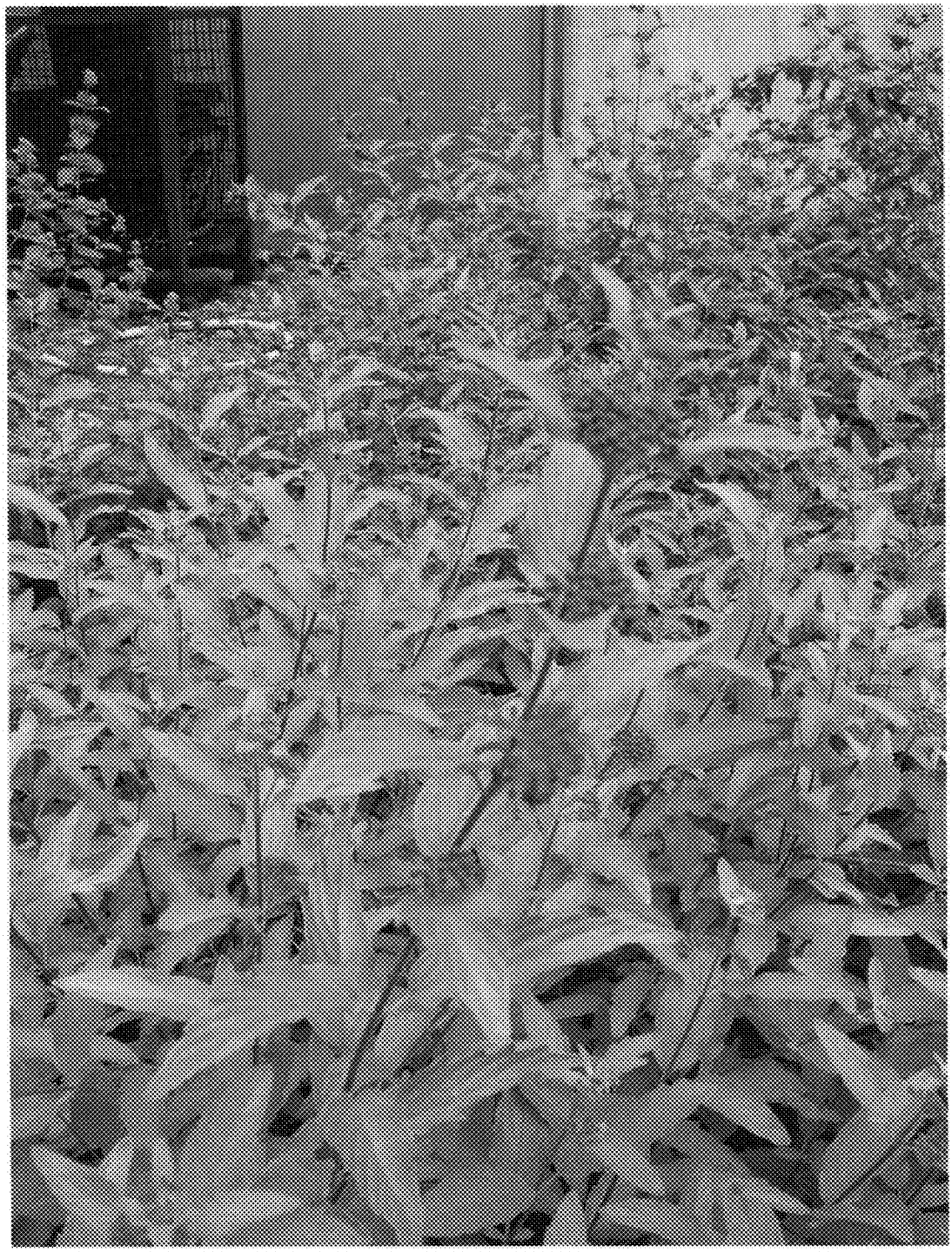

The drawing labeled as FIG. 2 depicts a close-up view of the flower buds and flowers of a planting of 'GOLD GIANT' in the ground in Hampshire, United Kingdom.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Caryopteris* cultivar named 'GOLD GIANT'. Observations, measurements, values and comparisons were collected in April from a 6-month-old 1-liter container plant growing out-of-doors in Arroyo Grande, Calif. Color determinations are made in accordance with The 2001 Royal Horticultural Society Colour Chart from London, England, except where general color terms of ordinary dictionary significance are used. The growing requirements of the new variety 'GOLD GIANT' are similar to the species.

Botanical classification: *Caryopteris*×*clandonensis* 'GOLD GIANT'.
Family: Verbenaceae.
Genus: *Caryopteris.*
Species: ×*clandonensis.*
Denomination: 'GOLD GIANT'.
Common name: Blue-mist or bluebeard.
Habit: Strong upright.
Commercial category: Ornamental shrub.
Use: Suitable for pots & containers, garden border, and modern landscape.
Suggested commercial container size: 1-liter container and larger.
Parentage: The new variety *Caryopteris*×*clandonensis* 'GOLD GIANT' is a seedling selection derived from the deliberate open cross-pollination of the seed parent an individual *Caryopteris clandonensis* 'Worcester Gold' and the pollen parent an individual *Caryopteris clandonensis* 'Worcester Gold'.
Propagation method: Semi-ripe stem cuttings
Rooting system: Fine.
Vigor: Vigorous.
Time to produce a 10 cm. container (range): 8-12 weeks from a 128 cell transplant.
Time to produce a 1-liter container (range): 12-16 weeks from a 128 cell transplant.
Dimensions first year (average): 60 cm. in height and 76 cm. in width.
Mature dimensions (average): 90 cm-110 cm. in height and 90 cm-110 cm. in width.
Cultural requirements: Performs best in full sun, with well-draining soil, and minimal to moderate water.
Disease and pest susceptibility: Susceptible to spider mites.
Disease and pest resistance: None known to the inventor.
Hardiness: USDA Zone 6.
Special considerations: Drought tolerant and heat tolerant once established. Cut back hard in spring to ensure good branch structure.

Stem:
- *Branching habit.*—Basal and lateral branching.
- *Lateral branch quantity* (*range*).—20-25 per 1-liter container plant.
- *Shape.*—Obcylindric.
- *Surface.*—Pubescent.
- *Color of mature stems.*—N200A.
- *Color of new growth stems.*—145C.
- *Stem length* (*average*).—6 cm.
- *Stem diameter* (*average*).—3 mm.
- *Stem strength.*—Flexible.
- *Internode* (*average*).—2 cm.
- *Stem fragrance.*—Aromatic.

Foliage:
- *Type.*—Deciduous.
- *Leaf arrangement.*—Opposite.
- *Leaf division.*—Simple.
- *Leaf quantity* (*average*).—26 per lateral stem.
- *Leaf margin* (*range*).—Irregularly toothed to crenate.
- *Leaf surface* (*abaxial*).—Pubescent.
- *Leaf surface* (*adaxial*).—Puberulent.
- *Leaf texture.*—Velvety.
- *Leaf shape* (*range*).—Lanceolate to ovate.
- *Leaf length* (*range*).—3.80 cm-5 cm.
- *Leaf width* (*range*).—3.10 cm-4 cm.
- *Leaf color* (*abaxial surface*).—147C.
- *Leaf color* (*adaxial surface*).—Ranges between 153A and 153D.
- *Venation pattern.*—Pinnate.
- *Vein color* (*abaxial surface*).—145C.
- *Vein color* (*adaxial surface*).—146C.
- *Leaf apex* (*range*).—Subacute to rounded.
- *Leaf base* (*range*).—Rounded to truncate.
- *Attachment.*—Petiolate.
- *Petiole surface.*—Pubescent.
- *Petiole shape.*—Sulcate.
- *Petiole color.*—145C.
- *Petiole dimensions* (*average*).—1 cm. in length and 1 mm. in diameter.
- *Durability of foliage to stress.*—Moderate.
- *Stipules.*—Present.
- *Stipule surface.*—Pubescent.
- *Stipule color.*—145C.
- *Stipule dimensions.*—<1 mm. in height and width.
- *Stipule shape.*—Ovate.
- *Leaf fragrance.*—Aromatic.

Inflorescence:
- *Type.*—Axial cyme.
- *Inflorescence quantity* (*average*).—>25 per 1-liter container plant?
- *Inflorescence dimensions* (*average*).—1.50 cm. in height and 2.5 cm in width.
- *Rate of opening.*—40% of inflorescence opens in 10 days.
- *Blooming months.*—June through October.

*Flower quantity* (*range*).—10-12 per inflorescence.
*Flower dimensions.*—1.15 cm. in depth and 0.50 cm. in diameter.
*Flower aspect.*—Upright to outward.
*Persistent or self-cleaning.*—Self-cleaning.
*Peduncle shape.*—Cylindric.
*Peduncle surface.*—Densely pubescent.
*Peduncle strength.*—Moderate.
*Peduncle color.*—145C.
*Peduncle dimensions* (*average*).—1 cm. in length and <1 mm. in diameter.
*Pedicel dimensions.*—2 mm. in length and <1 mm. in diameter.
*Pedicel color.*—145C.
*Pedicel strength.*—Moderate.
*Bud quantity* (*range*).—10-12 per inflorescence.
*Bud shape.*—Globular.
*Bud apex.*—Obtuse.
*Bud color.*—91B.
*Bud surface.*—Lanate.
*Bud dimensions.*—3 mm. in length and 3 mm. in diameter.
*Corolla shape.*—Bilabiate.
*Corolla dimensions.*—1.15 cm. in depth and 0.50 cm. in diameter.
*Corolla longevity on plant* (*average*).—12 days.
*Corolla tube dimensions.*—6 mm. in length and 2 mm. in width.
*Corolla tube color* (*range*).—91B-91C.
*Corolla lobe.*—5 in number.
*Corolla lobe color* (*ventral surface*).—92D.
*Corolla lobe color* (*dorsal surface*).—92A.
*Corolla lobe surface* (*ventral and dorsal*).—Pubescent.
*Corolla lobe length* (*range*).—3-6 mm.
*Corolla lobe width* (*range*).—2-3 mm.
*Corolla lobes fused or unfused.*—Basally fused.
*Corolla lobe margin* (*range*).—Entire to fimbriate.
*Corolla lobe shape* (*range*).—Concave to spreading.
*Corolla lobe apex* (*range*).—Acute to truncate.
*Calyx shape.*—Deeply lobed.
*Calyx color.*—146B.
*Calyx dimensions.*—0.40 cm. in length and 3 mm. in width.
*Sepals.*—5 in number.
*Sepal shape.*—Narrow elliptic.
*Sepal dimensions.*—3 mm. in length and <1 mm. in width.
*Sepals fused or unfused.*—Basally fused.
*Sepal color* (*ventral and dorsal surface*).—146B.
*Sepal margin.*—Entire.
*Sepal apex.*—Acute.
*Sepal surface* (*abaxial and adaxial*).—Lanate.
*Inflorescence fragrance.*—Aromatic.

Reproductive organs:
*Stamen quantity.*—4 in number.
*Stamen length.*—10 mm, exserted.
*Stamen color.*—92B.
*Anther color.*—N138A.
*Anther length.*—<1 mm.
*Pollen.*—Slight amount, color: 95A.
*Pistil quantity.*—1 in number.
*Pistil length.*—14 mm.
*Pistil color.*—93C.
*Stigma shape.*—Bifid.
*Stigma color.*—93C.
*Stigma diameter.*—3 mm.
*Ovary position.*—Superior.
*Ovary color.*—146C.
*Ovary dimensions.*—<1 mm in height and <1 mm. in width.
*Ovary shape.*—Globular.
*Ovary surface.*—Glabrous.

I claim:

1. A new and distinct cultivar of *Caryopteris* plant named 'GOLD GIANT' as described and illustrated herein.

* * * * *